United States Patent
Parent

(10) Patent No.: US 9,687,269 B2
(45) Date of Patent: Jun. 27, 2017

(54) HEMODIALYSIS DOUBLE LUMEN NEEDLE ANGIO CATHETER

(71) Applicant: Theresa Ann Parent, Surrey (CA)

(72) Inventor: Theresa Ann Parent, Surrey (CA)

( * ) Notice: Subject to any disclaimer, the term of this patent is extended or adjusted under 35 U.S.C. 154(b) by 336 days.

(21) Appl. No.: 14/523,342

(22) Filed: Oct. 24, 2014

(65) Prior Publication Data

US 2016/0113677 A1  Apr. 28, 2016

(51) Int. Cl.
*A61B 17/34* (2006.01)
*A61M 1/36* (2006.01)
*A61M 25/00* (2006.01)

(52) U.S. Cl.
CPC ...... *A61B 17/3417* (2013.01); *A61B 17/3403* (2013.01); *A61M 1/3661* (2014.02); *A61M 25/0084* (2013.01); *A61B 2017/3454* (2013.01); *A61M 2025/0091* (2013.01)

(58) Field of Classification Search
CPC ............ A61B 17/3417; A61B 17/3403; A61B 2017/3454; A61B 17/3421; A61B 17/3423; A61M 1/3661; A61M 25/0084; A61M 2025/0091
See application file for complete search history.

(56) References Cited

U.S. PATENT DOCUMENTS

| 4,099,528 A | 7/1978 | Sorenson |
| 4,403,983 A | 9/1983 | Edelman |
| 4,770,652 A * | 9/1988 | Mahurkar ........... A61M 5/1582 604/272 |
| 4,921,479 A | 5/1990 | Grayzel |
| 5,797,869 A | 8/1998 | Martin |
| 7,833,214 B2 | 11/2010 | Wilson |
| 8,529,544 B2 | 9/2013 | Haarala |
| 8,845,590 B2 | 9/2014 | Ash |
| 2006/0189922 A1* | 8/2006 | Amarasinghe .... A61M 25/0026 604/28 |
| 2007/0078438 A1 | 4/2007 | Okada |
| 2007/0250011 A1* | 10/2007 | Lee ................... A61M 25/0606 604/165.03 |

(Continued)

FOREIGN PATENT DOCUMENTS

| CA | 1111733 | 11/1981 |
| CA | 1222177 | 5/1987 |

(Continued)

*Primary Examiner* — Bhisma Mehta
*Assistant Examiner* — Hamza Darb
(74) *Attorney, Agent, or Firm* — Mark Terry

(57) ABSTRACT

An angio catheter for hemodialysis is disclosed. The angio catheter comprises a steel cylindrical element for introducing into a patient's blood vessel. The invention also includes a needle including a first lumen and a second lumen, each lumen hermetically separate from the other, wherein the needle is located within the cylindrical element. The invention further includes a first tube for supplying fluid to or from the first lumen and a second tube for supplying fluid to or from the second lumen, wherein fluid may flow within the first lumen independently from fluid flowing within the second lumen. The invention also includes a first flange extending perpendicularly from both sides of the cylindrical element and a second flange extending perpendicularly from both sides of an offset neck of the needle.

19 Claims, 5 Drawing Sheets

(56) References Cited

U.S. PATENT DOCUMENTS

2008/0208133 A1* 8/2008 Lieberman ........ A61M 25/0668
604/171
2009/0204079 A1 8/2009 Nimkar

FOREIGN PATENT DOCUMENTS

| CA | 1330285 | 6/1994 |
| CA | 2320377 | 7/2008 |
| CA | 2432330 | 9/2009 |
| CA | 2741897 | 12/2011 |
| EP | 00255704 | 10/1983 |
| EP | 1006885 | 6/2000 |
| WO | 2009123729 | 10/2009 |

\* cited by examiner

HEMODIALYSIS DOUBLE LUMEN NEEDLE ANGIO CATHETER

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

This relates to the field of catheters, and more specifically to the field of catheters used for hemodialysis.

BACKGROUND

Hemodialysis is a process that uses a man-made membrane, known as a dialyzer, to remove wastes, such as urea, from the blood. For hemodialysis, a patient is connected to a filter or dialyzer by tubes attached to a patient's blood vessels. Blood is then slowly pumped from the body into the dialyzer, where waste products and extra fluid are removed. The filtered or cleansed blood is then pumped back into the patient's body.

Traditionally, the double-needle treatment hemodialysis procedure requires one needle for blood flowing out of the body into the filter or dialyzer and a second needle to return the cleansed blood back to the patient's body. This flow of blood is continuous over the course of the hemodialysis treatment. The average treatment duration is four hours approximately three times per week. The needles are strategically placed on the body apart from each other.

Single needle treatment also exists. Single needle treatment requires a different type of apparatus that allows blood to flow intermittently. In such treatments, blood is removed and returned using a single needle with a slight pause in between blood flowing into the body and blood flowing out of the body. However, this decreases the efficiency of each treatment. As a result, single needle treatment is not widely used and the double needle treatment is more commonly utilized, requiring two punctures per treatment.

Double punctures every time a patient treats with double needle treatment causes twice as much trauma as with single needle treatment dialysis. Additionally, the amount of waste resulting from the double punctures when two needles are used is more than that when single needle treatment is used. As mentioned above, another problem associated with the current single needle treatment design is recirculation. The recirculation of previously dialyzed blood in the lumen of the single-needle catheter reduces dialysis efficiency and is a drawback of single-needle dialysis. Because of recirculation associated with single-needle treatments, it may be necessary to increase the amount of time that a patient is required to be connected to the dialyzer, which results in an inconvenience to the patient.

Therefore, a need exists to overcome the problems with the prior art, and more specifically a better method or device for hemodialysis treatments.

SUMMARY

In one embodiment, an angio catheter for hemodialysis is disclosed. The angio catheter comprises a steel cylindrical element for introducing into a patient's blood vessel. The invention also includes a needle including a first lumen and a second lumen, each lumen hermetically separate from the other, wherein the needle is located within the steel cylindrical element. The invention further includes a first tube for supplying fluid to or from the first lumen and a second tube for supplying fluid to or from the second lumen, wherein fluid may flow within the first lumen independently from fluid flowing within the second lumen. The invention also includes a first flange extending perpendicularly from both sides of the steel cylindrical element and a second flange extending perpendicularly from both sides of an offset neck of the needle.

In another embodiment, the needle comprises a first end opposing a second end, the needle further comprising at least one opening proximate to said second end allowing access into the first lumen. In a further embodiment, the steel cylindrical element is tapered at its second end forming a point, and the second end further comprises a sharp edge for facilitating puncture of a blood vessel.

Additional aspects of the disclosed embodiments will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION

Figure 1:
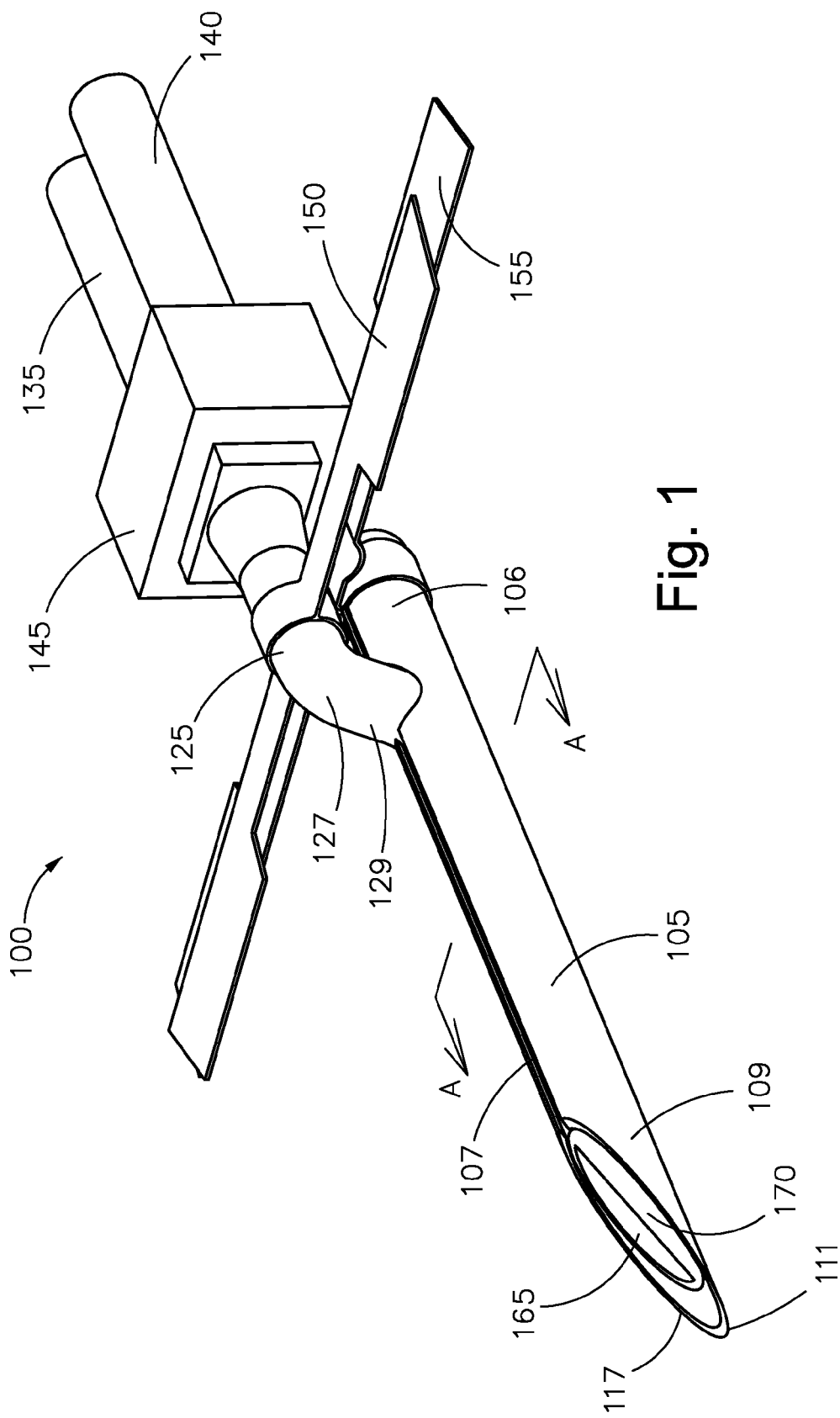
FIG. 1 is a perspective view of a double lumen needle angio catheter, in accordance with one embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering, or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a double lumen needle angio catheter that is easy to use and has a simple construction. The disclosed embodiments provide a device that reduces the amount of punctures a patient must endure during hemodialysis while still providing efficient hemodialysis. Additionally, the amount of needles needed or required for hemodialysis is thereby also reduced by about 50% over double puncture scenarios. Additionally, the proposed needle may also reduce the amount of time that a patient is required to be connected to a dialysis unit.

FIG. 1 is a perspective view of the catheter 100, in accordance with one embodiment. One of the purposes of the catheter is to provide two chambers to allow independent flow of blood in and out of a single device. The catheter comprises a steel cylindrical element 105 (or sleeve) for introducing into a patient's blood vessel. The cylindrical element defines a cylindrical hollow shaped body having a first end 106 opposing a second end 109. The cylindrical element's body has an elongated slot 107 spanning from the first end to the second end. The steel cylindrical element may be formed from material capable of safe insertion into an individual's body, such as surgical grade steel, or other composites used for puncturing the skin and blood vessels. The second end of the cylindrical element is tapered forming a point 111. The second end further includes an edge 117 for facilitating puncture of a blood vessel. The edge may be ground to form a sharp edge adapted for puncturing skin and blood vessels. The taper of the cylindrical element may be adjusted depending on the use and may define various oblique angles. Traditional methods and apparatus of forming surgical grade lumens may be used in forming the cylindrical element.

The needle 121 has an elongated hollow shaped cylindrical body 120 having a circumference and having a first end 125 opposing a second end 130. The length of the needle is sized such that the second end 109 of the cylindrical element extends beyond the second end of the needle so that the second end of the cylindrical element punctures the skin and blood vessel. The needle and cylindrical element's gauge and design is adapted to coincide with the standard blood flow for hemodialysis treatment. The outside cross-sectional diameter of the body 120 of the needle is sized so that it is slightly less than the internal cross-sectional diameter of the body 105 of the cylindrical element. This allows the body 120 of the needle to snugly fit within the body of the cylindrical element.

In one embodiment, the first end 125 of the needle defines a neck 127 offset from the longitudinal axis of the body of the needle. The neck 127 is connected to the body by an attaching member 129 that extends outward from the body 120 of the needle. The slot 107 of the cylindrical element is adapted in size and shape to allow the attaching member of the needle to pass such that the needle can be slid within the cylindrical element. The slot also allows for the removal of the cylindrical element after the needle is inserted into the blood vessel and so that the needle may be slid out of the cylindrical element. This facilitates for allowing the inner needle to remain inside of an individual's blood vessel during the course of treatment and for allowing to more easily remove a needle and its associated tubes from an individual. The second end of the needle is also tapered to match the taper of the second end of the cylindrical element. The needle may be formed from any material capable of sterilization such as surgical grade steel, polymer based plastics, composites, any combination thereof, etc.

Figure 2:
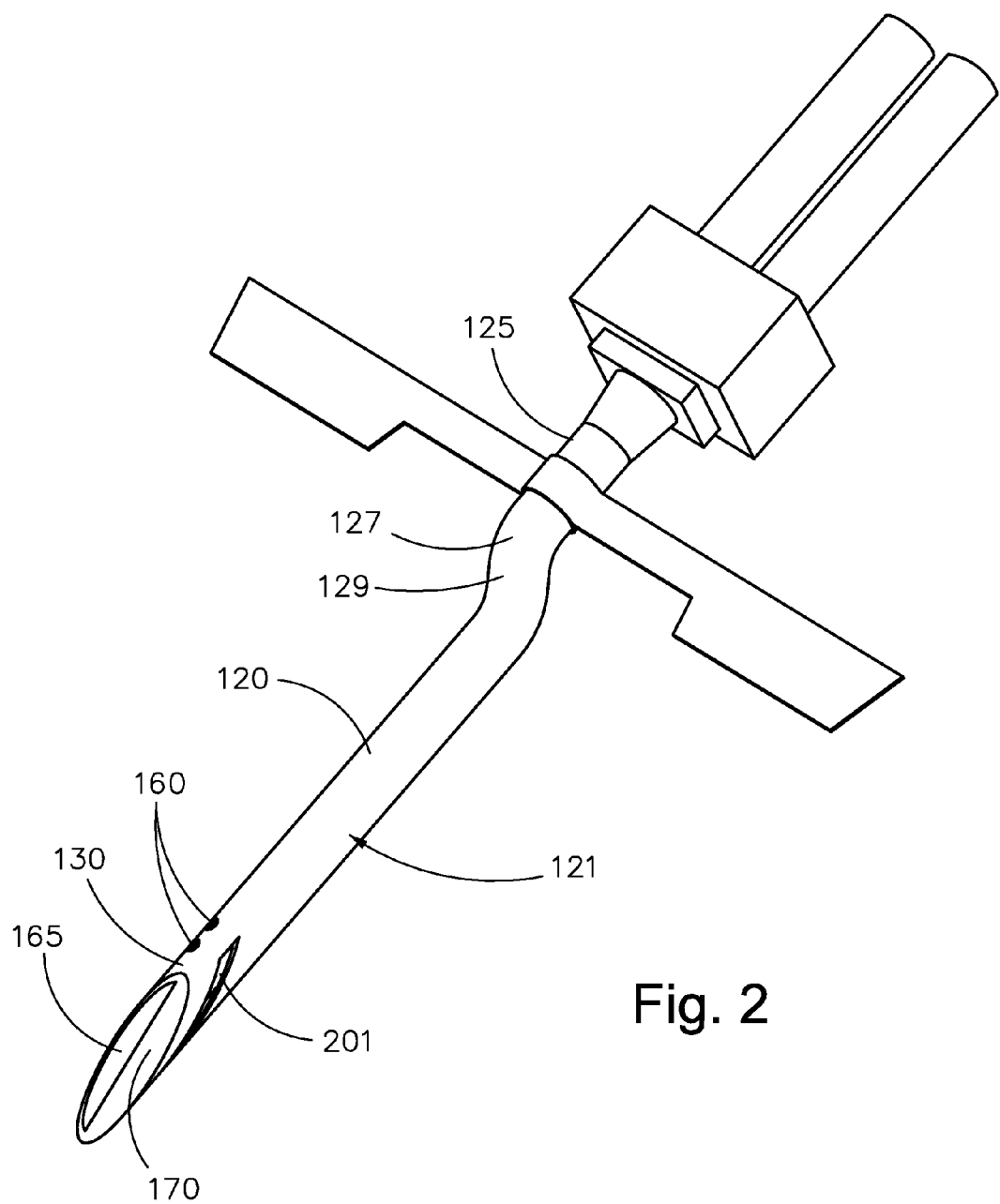
FIG. 2 is another perspective view of a double lumen needle angio catheter, in accordance with another embodiment.
Figure 2A:
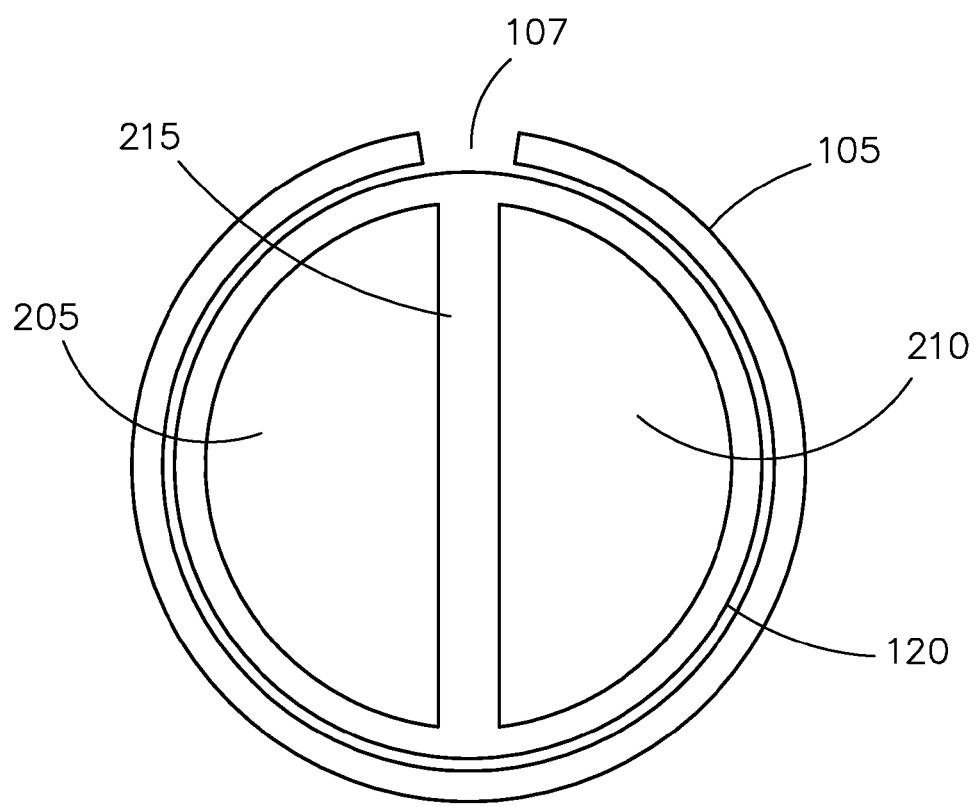
FIG. 2A is a cross-sectional view of a needle of the double lumen needle angio catheter, in accordance with one embodiment.

FIG. 2 is another perspective view of the catheter in accordance with a different embodiment. Note that FIG. 2 is only an exemplary embodiment that illustrates one possible embodiment of the catheter. In this embodiment, the needle 120 has a first end 125 without an offset neck or attaching member. FIG. 2A is a cross-sectional view taken from cross-sectional line A on FIG. 2. FIG. 2A illustrates the cylindrical needle body 120 within the cylindrical element body 105. The needle includes a first lumen 205 opposing a second lumen 210 separated by a sternum or wall 215. The sternum or wall spans from the first end to the second end of the needle and hermetically separates the first lumen from the second lumen such that fluid may flow within the first lumen independently from fluid flowing from the second lumen.

Referring back to FIG. 1, the first end 125 of the needle is connected to a pair of tubes. The first tube 135 is connected to the first lumen 205 and is for supplying fluid to or from the first lumen. The second tube 140 is connected to the second lumen 210 and is for supplying fluid to and from the second lumen. A second end of each of these tubes may be connected to the dialysis or hemodialysis machine. During treatment, fluid or blood it may be pumped in and out of each of these lumens. The sternum or wall separating the first and second lumen also facilitates the blood to flow in and out with minimal recirculation.

FIG. 1 also illustrates a main opening 165 (having a roughly semicircular shape) at the second end of the needle that provides access into the first lumen. Also shown is a pair of openings 160 along the body of the needle proximate to second end 130 of the needle body provides additional access to the first lumen. In the present embodiment, each of the openings 160 is circular in shape and allows access into the first lumen. The shape and size of each opening and the amount of openings may be changed or adapted depending on the amount of flow that is required or needed in or out of the first lumen.

FIG. 1 also illustrates a barrier 170 that blocks access into the second lumen 210 at the second end of the needle. The barrier is adapted to prevent access from the second end of the needle into the second lumen. The barrier may be flush with the second end of the lumen and sternum or wall. Fluid may flow in and out of the second lumen through an elongated slot 201 (shown in FIG. 2) proximate to the second end of the needle behind the barrier. As shown in FIG. 2, the elongated slot may be roughly rectangular in shape. The elongated slot may vary in size depending the amount of flow required to enter or exit the second lumen 210. The elongated slot and barrier facilitate in minimizing recirculation of blood flow during treatment.

An adapting element 145 may connect the pair of tubes to the first end 125 of the needle. In the present embodiment, the adapting element is a cubed shaped body positioned in between the pair of tubes and the second end 125 of the needle. The inside of the adapting element (not shown) provides a transition and allows for an end of the first tube to be connected to the first lumen 205 at the first end of the needle. Similarly, the inside of the adapting element also provides a transition for allowing an end of the second tube to be connected to the second lumen 210 at the first end of the needle. In another embodiment (not shown), no adapting element is needed. In such an embodiment, the first end of the needle is adapted such that the first and second lumens may be connected directly to ends of the first and second tubes, respectively. Also shown in FIG. 1 is a first flange 150 and a second flange 155 for facilitating handling of the needle and cylindrical element (more specifically explained in FIGS. 3-4).

Figure 3:
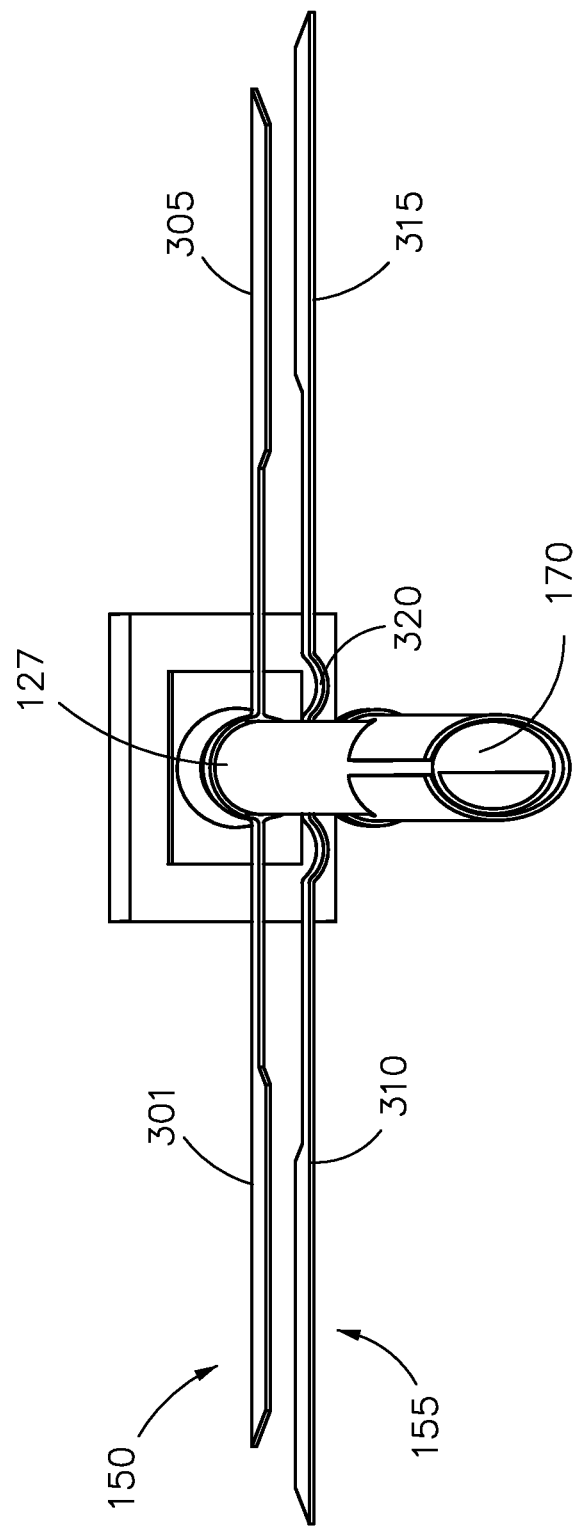
FIG. 3 is a front view of a double lumen needle angio catheter, in accordance with one embodiment.

FIG. 3 is a front view of the catheter in accordance with one embodiment. FIG. 3 further illustrates the first 155 and second 150 flanges. In the present embodiment, the first flange is rotatably attached near or proximate to the second end 125 of the offset neck 127 of the needle. The first flange extends perpendicularly from the offset neck of the needle. In FIG. 3, the first flange is in an open position such that the first flange comprises a first arm 301 extending perpendicularly from a side of the neck of the needle and a second arm 305 extending perpendicularly from a second opposing side of the neck of the needle. The first flange facilitates handling of the needle.

Figure 4:
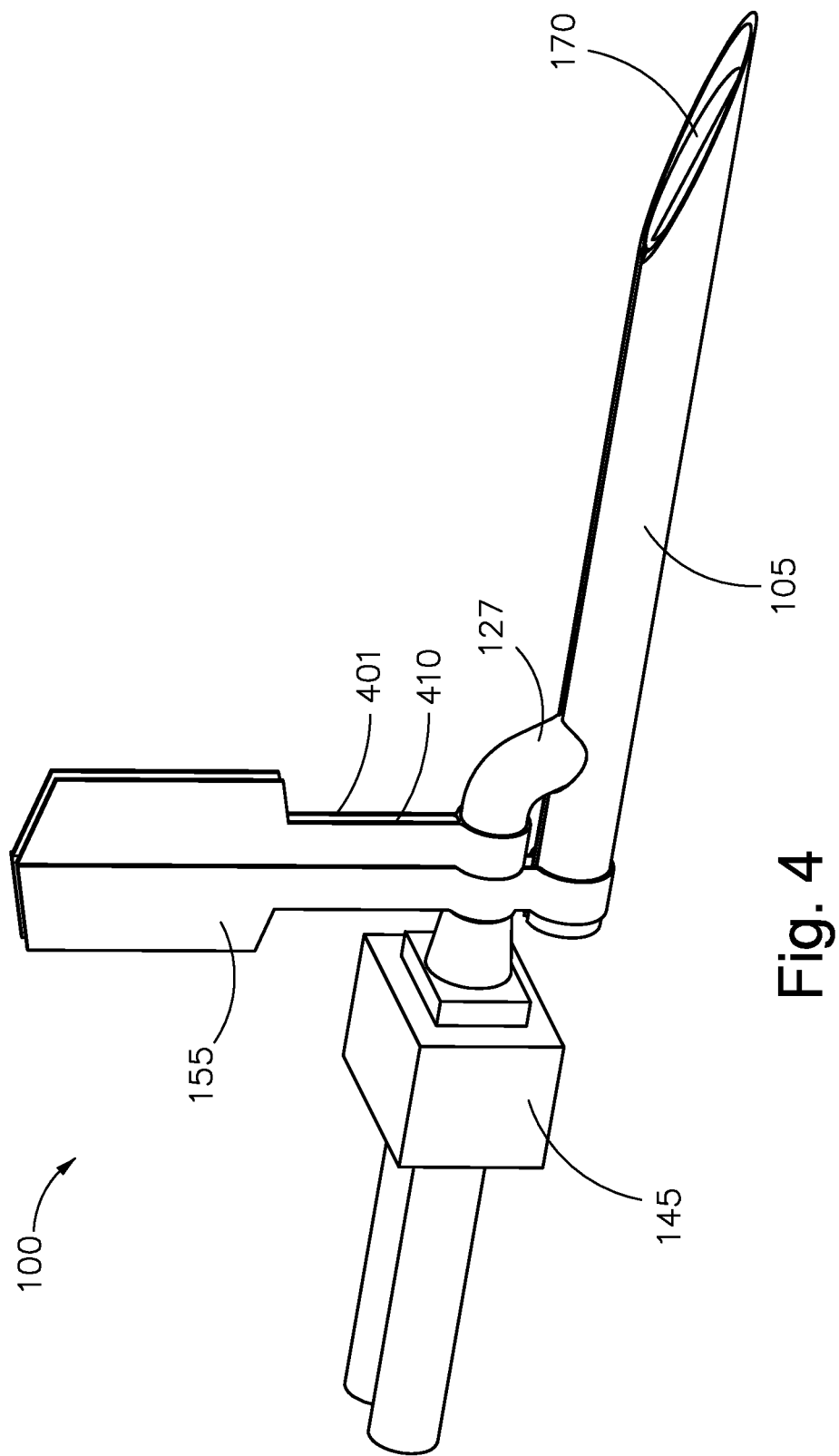
FIG. 4 is a side view of a double lumen needle angio catheter, in accordance with one embodiment.

The second flange 150 is attached proximate to the first end 106 of the cylindrical element. In FIG. 3, the second flange is in an open position such that the second flange has a first arm 310 on a side of the cylindrical element and a second arm 315 on an opposing side of the cylindrical element. Each arm of both the first and second flanges is an elongated rectangular planar shape. Each arm of the second flange further defines a semicircular depression 320 adapted such that when the arms are rotated so that a surface of the first arm contacts a surface of the second arm (as shown in FIG. 4), each depression receives a portion of the offset neck 127 of the needle. The second flange is also attached such that in the open position, as shown in FIG. 3, the first and second arms of the second flange do not obstruct the slot 107 of the cylindrical element. In the closed position, the needle may be maneuvered in and out of the cylindrical element via the slot. The flanges may comprise any material that capable of sterilization such as surgical grade steel, polymer based plastics, composites, any combination thereof, etc.

FIG. 4, is a side perspective view of the catheter, in accordance with one embodiment. FIG. 4 illustrates the catheter with the cylindrical element 105 sheathing the needle 120. FIG. 4 also illustrates the first 155 and second 150 flanges in their closed positions. In its closed position, the arms of the first flange are rotated to a topside of the needle such that a surface of the first arm abuts a surface of the second arm. In other embodiments, the arms of the first flange may be rotated to other sides of the offset neck 127 such that they only extend from one side of the offset neck. The first flange has a rectangular shaped cutout 410 from along the edge of each of its arms.

In its closed position, the arms of the second flange are rotated such that the depressions 320 (shown in FIG. 3) of the arms of the second flange receive opposing sides of the offset neck of the needle. In this position, the flanges assist a user in the maneuvering and handling the catheter. Additionally, in the closed position, the arms of the second flange maintain the cylindrical element with the remainder of the catheter by preventing the needle from sliding within the cylindrical element. The second flange further comprises a rectangular shaped cutout 401 from each of its arms.

The actual operation of one embodiment will be described. In FIG. 1, an end of the first tube 135 and an end of the second tube 140 are attached to and adapting element 145, which connects to the first end 125 of the needle. The second of the tubes are connected to a dialysis unit (not shown). The adapting element provides a transition for the flow of fluid to and from the first and second tubes to the first 205 and second 210 lumens, respectively.

In the closed flange position, as shown in FIG. 4, the arms of the second flange 150 are rotated such that a surface of both the first and second arms of the second flange abut the other and such that the depressions 320 (shown in FIG. 3) of the second flange receive the offset neck 127 of the needle. In this position, the needle is held within and partially surrounded by the cylindrical element. To insert into a person's blood vessel, force is applied so that the sharp edge 117 and point 111 of the cylindrical element puncture the person's blood vessel. This allows fluid or blood to flow in and out of the first and second lumens. After insertion into a person's blood vessel, the second flange may be rotated into an open position, as shown in FIG. 1, to allow either the lumen or the needle to be removed. To remove, the needle or cylindrical element can be slid out of the blood vessel. In certain medical situations, it is beneficial to have the inner needle remain in a person's blood vessel throughout the entire treatment. This allows medical professionals to insert medication or blood into a blood vessel without having to re-puncture a person. During treatment, the blood flows to and from the first and second lumens through the openings 165, 160 and slot 201 along the body of the needle.

Although specific embodiments of the invention have been disclosed, those having ordinary skill in the art will understand that changes can be made to the specific embodiments without departing from the spirit and scope of the disclosed embodiments. The scope of the invention is not to be restricted, therefore, to the specific embodiments. Furthermore, it is intended that the appended claims cover any and all such applications, modifications, and embodiments within the scope of the disclosed embodiments.

What is claimed is:

1. An angio catheter, comprising:
    a steel cylindrical element for introducing into a patient's blood vessel, wherein the cylindrical element further comprises a first end opposing a second end;
    a needle including a first lumen and a second lumen, wherein the first lumen is hermetically separate from the second lumen, wherein the needle is located within the cylindrical element such that the needle slides within the cylindrical element, and wherein the needle comprises a first end opposing a second end;
    the needle having a neck offset from a longitudinal axis of the needle, wherein the neck connects to the first end of the cylindrical element;
    a first tube for supplying fluid to or from the first lumen;
    a second tube for supplying fluid to or from the second lumen;
    a first flange extending perpendicularly from the cylindrical element, wherein when the flange is in a closed position, the flange receives the needle and prevents the needle from sliding within the cylindrical element;
    a first flange extending perpendicularly from the neck of the needle;
    and
    wherein fluid flows within the first lumen independently from fluid flowing within the second lumen.

2. The angio catheter of claim 1, the needle further comprising at least one opening proximate to said second end of the needle allowing access into the first lumen.

3. The angio catheter of claim 2, wherein the needle further includes a barrier at the second end of the needle preventing access into the second lumen, said second end of the needle having a slot behind said barrier allowing access into said second lumen, and the needle being tapered at the second end of the needle forming a point.

4. The angio catheter of claim 3, wherein the needle is tapered at the second end of the needle forming a point.

5. The angio catheter of claim 3, wherein the second flange facilitates handling of the needle.

6. The angio catheter of claim 3, wherein an adapting element connects the first tube with the first lumen and connects the second tube with the second lumen.

7. The angio catheter of claim 1, wherein the needle further defines a circumference, and wherein the steel cylindrical element is adapted for partially surrounding the circumference of the needle.

8. The angio catheter of claim 1, wherein the cylindrical element further having an elongated slot spanning from said first end of the cylindrical element to said second end of the cylindrical element of the cylindrical element, said slot adapted for receiving the needle and allowing removal of cylindrical element after the needle is inserted into a blood vessel.

9. The angio catheter of claim 8, wherein the second end of the steel cylindrical element extends beyond the second end of the needle.

10. The angio catheter of claim 8, wherein the steel cylindrical element is tapered at the second end of the cylindrical element forming a point, and the second end of the cylindrical element further comprises a sharp edge for facilitating puncture of a blood vessel.

11. The angio catheter of claim 8, wherein the first flange is proximate to the first end of the cylindrical element and facilitates handling of the cylindrical element.

12. The angio catheter of claim 1, wherein the second flange is rotatably attached to the neck.

13. The angio catheter of claim 1, wherein the first flange is rotatably attached to the cylindrical element.

14. An angio catheter, comprising:
a steel cylindrical element for introducing into a patient's blood vessel, wherein the cylindrical element further comprises a first end opposing a second end;
a needle having a first end opposing a second end and including a first lumen and a second lumen, wherein the first lumen is hermetically separate from the second lumen by a sternum, and wherein the needle is located within the cylindrical element such that the needle slides within the cylindrical element, and wherein
the needle having a neck offset from a longitudinal axis of the needle, wherein the neck connects to the first end of the cylindrical element;
wherein the cylindrical element further includes an elongated slot spanning from said first end of the cylindrical element to said second end of the cylindrical element of the cylindrical element, said slot adapted for receiving the needle;
a first tube for supplying fluid to or from the first lumen;
a second tube for supplying fluid to or from the second lumen;
a first flange extending perpendicularly from the cylindrical element, wherein when the flange is in a closed position, the flange receives the needle and prevents the needle from sliding within the cylindrical element;
a second flange extending perpendicularly from the neck of the needle;
wherein fluid flows within the first lumen independently from fluid flowing within the second lumen;
wherein the needle has a set of openings proximate to said second end of the needle allowing access into the first lumen;
wherein the needle further having a barrier at the second end of the needle preventing access into the second lumen, said second end having a slot behind said barrier allowing access into said second lumen, and the needle being tapered at the second end of the needle forming a point.

15. The angio catheter of claim 14, wherein the second end of the steel cylindrical element extends beyond the second end of the needle, wherein the steel cylindrical element is tapered at the second end of the cylindrical element forming a point, the second end of the cylindrical element further having a sharp edge for facilitating puncture, and wherein the needle is tapered at the second end of the needle forming a point.

16. The angio catheter of claim 15, wherein the second flange facilitates handling of the needle, the second flange being rotatably attached to the neck, wherein the first flange is positioned proximate to the first end of the cylindrical element and facilitates handling of the cylindrical element, the first flange being rotatable attached to the cylindrical element.

17. An angio catheter, comprising:
a steel cylindrical element for introducing into a patient's blood vessel, wherein the cylindrical element further comprises a first end opposing a second end;
a needle including a first lumen and a second lumen, wherein the first lumen is hermetically separate from the second lumen, and wherein the needle is located within the cylindrical element such that the needle slides within the cylindrical element, and wherein the needle comprises a first end opposing a second end;
the needle having a neck offset from a longitudinal axis of the needle, wherein the neck connects to the first end of the cylindrical element;
a first tube for supplying fluid to or from the first lumen;
a second tube for supplying fluid to or from the second lumen;
a first flange extending perpendicularly from the cylindrical element, wherein when the flange is in a closed position, the flange receives the needle and prevents the needle from sliding within the cylindrical element; and
wherein fluid flows within the first lumen independently from fluid flowing within the second lumen.

18. The angio catheter of claim 17, wherein the needle further comprises at least one opening proximate to said second end of the needle allowing access into the first lumen, the needle further having a barrier at the second end of the needle preventing access into the second lumen, said second end of the needle having a slot behind said barrier allowing access into said second lumen, and the needle being tapered at the second end of the needle forming a point, the needle further defining a circumference, wherein the steel cylindrical element is adapted for partially surrounding the circumference of the needle, the cylindrical element further comprising an elongated slot spanning from said first end of the cylindrical element to said second end of the cylindrical element, said slot adapted for receiving the needle.

19. The angio catheter of claim 17, wherein the second end of the steel cylindrical element extends beyond the second end of the needle, wherein the steel cylindrical element is tapered at the second end of the cylindrical element forming a point, and the second end of the cylindrical element further comprising a sharp edge for facilitating puncture of a blood vessel, and wherein the needle is tapered at the second end of the needle forming a point.

* * * * *